United States Patent [19]

Shah et al.

[11] Patent Number: 5,208,015
[45] Date of Patent: May 4, 1993

[54] TOPICAL ANTI-FUNGAL AGENTS HAVING ANTI-INFLAMMATORY ACTIVITY

[75] Inventors: Hemanshu S. Shah; Cheng-Der Yu, both of Amherst; John Gibson, Buffalo, all of N.Y.

[73] Assignee: Bristol-Myers Squibb Company, New York, N.Y.

[21] Appl. No.: 734,701

[22] Filed: Jul. 23, 1991

[51] Int. Cl.$^5$ ............................................. A61K 9/10
[52] U.S. Cl. .................... 424/78.05; 514/171; 514/396; 514/880; 514/886
[58] Field of Search ............... 424/78.05; 514/396, 514/858, 944, 887, 886, 880, 171

[56] References Cited

U.S. PATENT DOCUMENTS

| | | | |
|---|---|---|---|
| 3,772,441 | 11/1973 | Lombardino | 514/396 |
| 4,013,792 | 3/1977 | Eichman et al. | 514/887 |
| 4,289,757 | 9/1981 | Glenn | 514/887 |
| 5,002,938 | 3/1991 | Wang et al. | 514/171 |
| 5,013,545 | 7/1991 | Blackman et al. | 514/887 |
| 5,028,418 | 7/1991 | Helman et al. | 514/858 |
| 5,087,620 | 2/1992 | Parab | 514/171 |

OTHER PUBLICATIONS

Remington's Pharmaceutical Sciences Treatise 17th Ed. (1985) Mack Publishing Co., p. 777.

Primary Examiner—Thurman K. Page
Assistant Examiner—D. Colucci
Attorney, Agent, or Firm—Sandra M. Nolan

[57] ABSTRACT

The certain imidazoles have been found to exhibit anti-inflammatory as well as antifungal activity.

11 Claims, 2 Drawing Sheets

TOPICAL ANTI-FUNGAL AGENTS HAVING ANTI-INFLAMMATORY ACTIVITY

BACKGROUND

Imidazoles, as a class, enjoy a reputation as antifungal agents. See L. Tanenbaum, et al, *Archives of Dermatology* — Vol. 120, (1984) pages 216-19, which reports a study of the effects of sulconazole and miconazole creams on *Tinea Versicolor*. See also S. A. Qadripur, *Curr. Therapeutic Res., Vol.* 35, No. 5, (1984), pages 753-8. There, the research found that the use of sulconazole 1% cream along with sulconazole powder performed about as well as econazole 1% cream and powder in treating cutaneous dermatophytoses.

Among the imidazoles, compounds of formula I

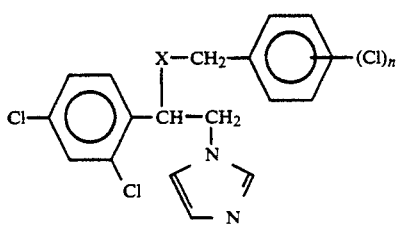

(I)

wherein $X = O$ or $S$ and $n = 1, 2$ or $3$, and their pharmaceutically acceptable derivatives, e.g. nitrate salts, have achieved a certain prominence where antifungal indications are concerned.

In a study of sulconazole nitrate cream versus clotrimazole cream for treating dermatophytoses, the sulconazole treated group showed faster systematic improvement. A. Lassus, et al *British Journal of Dermatology, 108,* (1983) pages 195-8.

In treating cutaneous candidiasis, sulconazole nitrate cream outperformed both its vehicle and miconazole nitrate cream. L. Tannebaum, et al., Int'l. Jour. of Dermatology, 22 (June, 1983), pages 318-20.

When compared to econazole in the treatment of dermatophytosis, sulconazole gave faster and more complete relief to patients. A. Lassus, et al, *Mykosen 27,* Heft. 12, (1984), pages 594-98.

The use of imidazoles in combination with steroids to treat fungal infections is well known. It is believed that the steroids work during the first few days of treatment to quiet inflammation, while the imidazoles work in several (i.e., generally 3 to 5) weeks to eliminate the fungal agent(s).

British specification 1474510 (published May 25, 1977,) describes ointments containing both imidazoles (as antifungals) and steroids (as anti-inflammatories). Likewise, U.S. Pat. No. 4,298,604 deals with antifungal formulations which contain clotrimazole and betamethasone dipropionate.

U.S. Pat. No. 5,002,938 discloses topical antifungal gels containing imidazoles and 17-ester corticosteroids useful for treating fungal infections.

Interestingly, the use of imidazoles alone to treat inflammations has not been directly studied. There have, however, been reports of work on the immunologic effects of a few imidazoles.

E. Drouket, et al, in *Zentrobl, Baktenol, Mikrobiol Hyg.,* Suppl. 13, (1985) pages 1-37 disclosed that ketoconazole is an immunomodulating drug, with responses being dose dependent. Miconazole was shown to have a suppressive effect on delayed type hypersensitivity, so that it may be of use in transplantation cases.

Also, K. Watanabe, et al, reported in *Pharmacometrics* (Japan), vol. 29, No. 4 (1985), pages 501-15, the immune, phototoxic and photoallergenic responses of guinea pigs to sulconazole administered in various forms.

The enzymes, 5-lipoxygenase and cyclooxygenase, catalyze the formation of leukotrienes which are important mediators of inflammation. D. Steinhilber et al, in Arzneim.-Forsch./Drug Res., vol. 40, No. 11 (1990), pages 1260-1263 reported that itraconazole, inhibited 5-lipoxygenase but not cycloxygenase, in an in vitro cell culture experime,nt. However, none of the other azoles tested, i.e., fluconazole, ketokonazole and miconazole, were significantly active in this model.

All disclosures referred to herein are hereby incorporated by reference.

THE INVENTION

It has been discovered that certain imidazoles, and their pharmaceutically acceptable salts, demonstrate, within the first week of topical administration, anti-inflammatory effects. These effects are in addition to the antifungal effects for which imidazoles are generally well-known.

Thus, the compounds, compositions and processes of the invention need be used for only about 2 to about 7 days, preferably about 3 to about 5 days, for anti-inflammatory effects to occur.

In a preferred embodiment, a sulconazole gel containing 1% sulconazole in a vehicle containing SD alcohol 40, 1,2,6-hexanetriol, 2-ethyl-1,3-hexanediol, isopropyl myristate and other pharmaceutical excipients was applied twice-a-day for 6 weeks to an area of skin exhibiting the effects of tinea pedis infection (athlete's foot). Within 1 to 3 days, the itching, burning/stinging and pain/tenderness had been substantially reduced. This was accompanied by a moderate reduction in the redness (erythema). Within one week, the itching, burning/stinging and pain/tenderness had been almost eradicated. Within six weeks, the fungal infection was gone. The data shown in FIGS. 1-4 demonstrates that sulconazole was as effective an anti-inflammatory agent as hydrocortisone valerate (HCV). HCV is a mid-potent steroid clinically used to treat inflammatory conditions of the skin.

OBJECTS OF THE INVENTION

It is an object of the invention to provide compositions useful for treating the inflammation normally associated with cutaneous fungal infection as well as the infections themselves.

It is another object to provide processes for treating such inflammation and such infections.

It is yet another object to provide materials and processes for both the treatment of the inflammation associated with fungal infections and the elimination of the fungal agent(s).

It is still a further object to provide a vehicle useful for compositions for treating inflammatory and/or fungal conditions.

ADVANTAGES

The compositions and processes of the invention have several advantages over other systems for treating inflammatory and fungal conditions.

Because they require no added anti-inflammatory agent(s), the systems of the invention are less expensive than e.g., steroid/imidazole or antibacterial/imidazole combinations. In addition, a system which does not contain steroids would avoid the side-effects of steroid therapy such as skin atrophy.

Furthermore, the compatibility problems often associated with putting two or more active ingredients in a formulation are avoided. For instance, special mixing procedures may be needed to insure adequate distribution of one or more of the active ingredients.

Lastly, the stability problems which generally occur when drug combinations containing steroids are made are not encountered.

These and other objects and advantages will be apparent after a consideration of the following specification and claims.

BRIEF DESCRIPTION OF THE DRAWINGS

The date shown in FIGS. 1-4 demonstrates that sulconazole was as effective an anti-inflammatory agent as hydrocortisone valerate (HCV).

DESCRIPTION OF THE INVENTION

Figure 1:
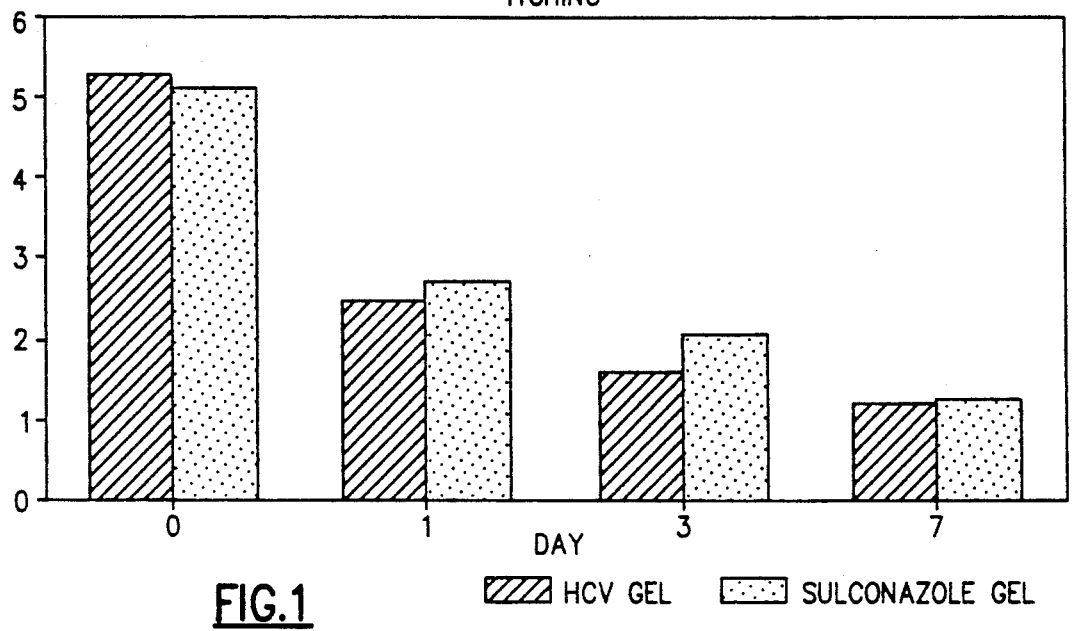
Figure 2:
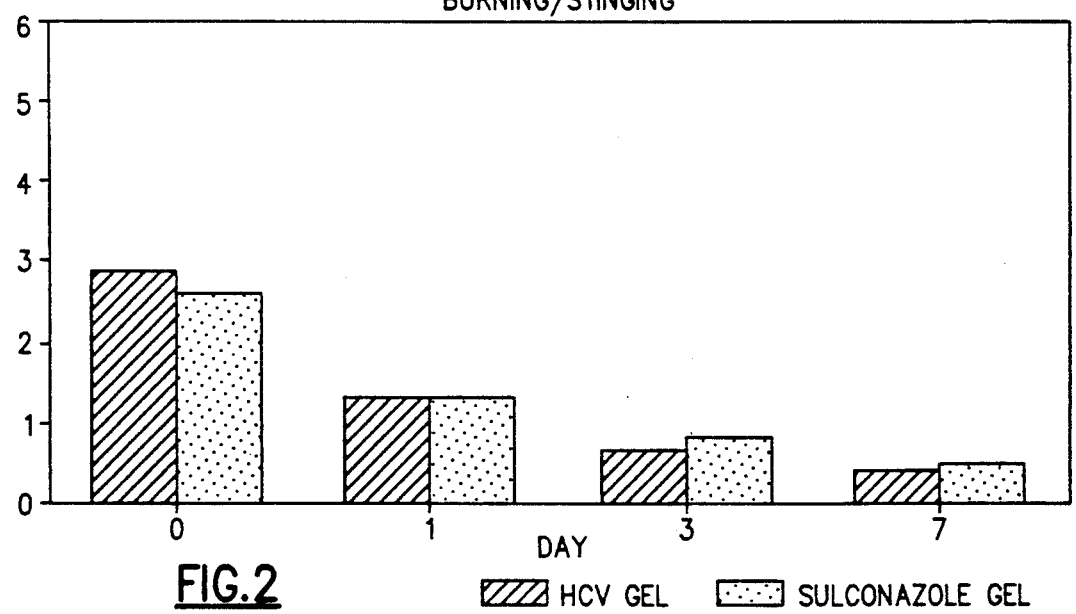
Figure 3:
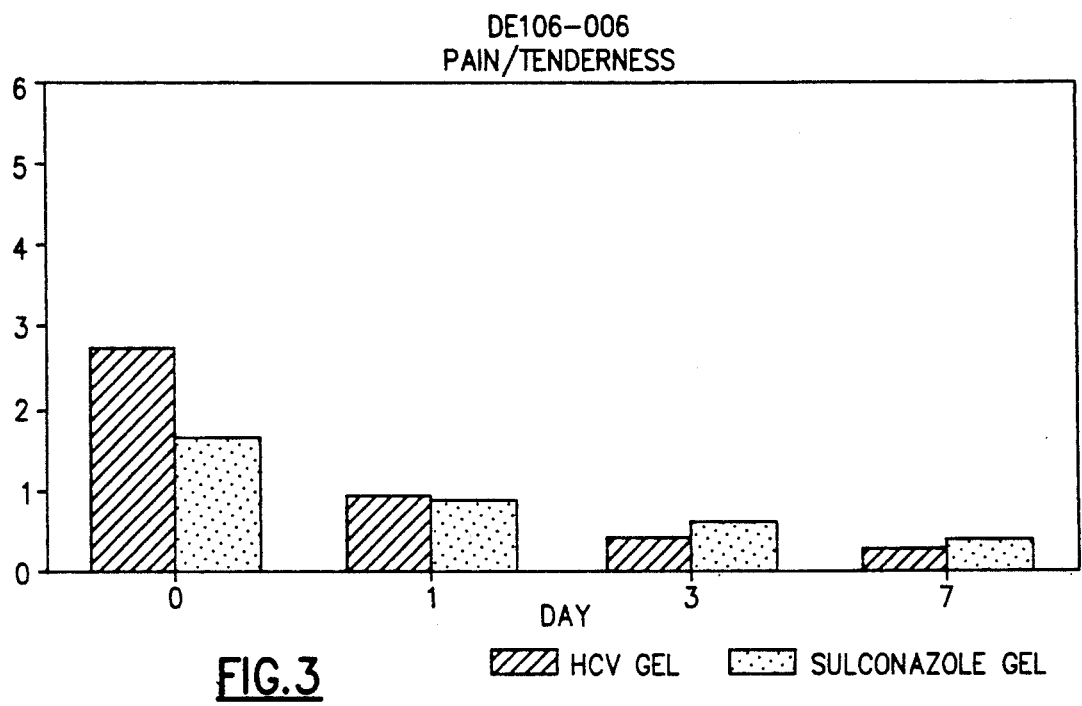
Figure 4:
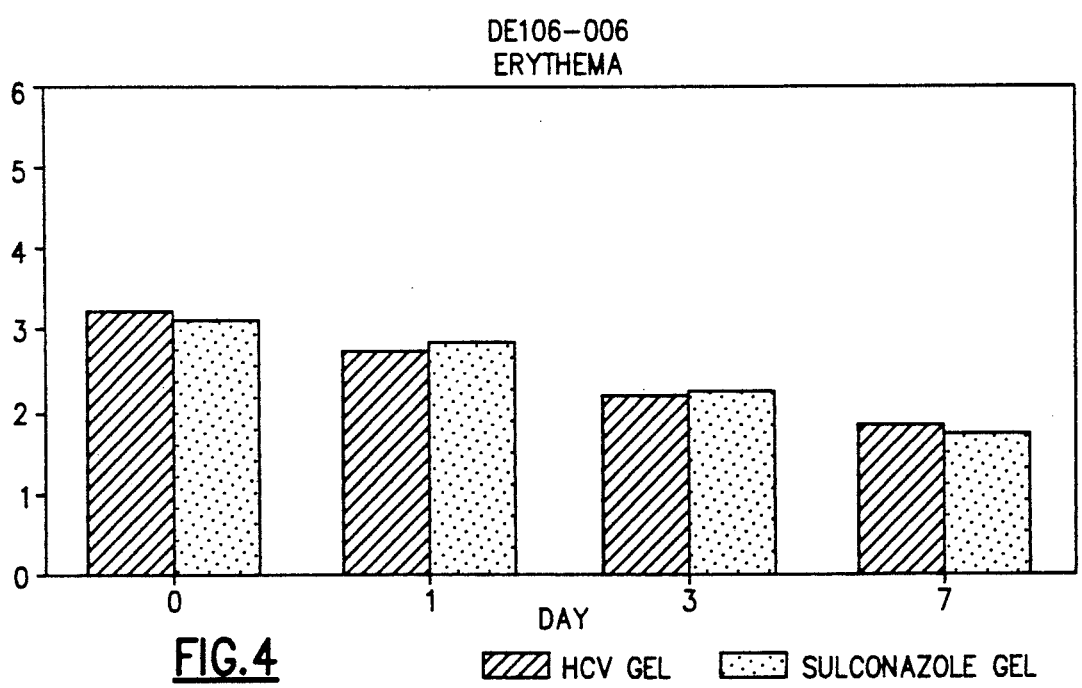

Unless otherwise indicated, all percentages recited herein are weight percentages, based on total composition weight.

COMPOUNDS

The useful compounds are generally those of formula I:

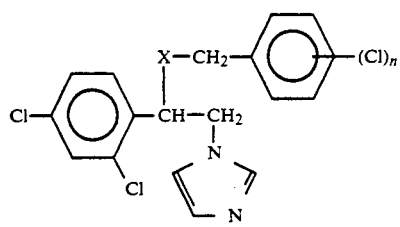

wherein X = O or S and n = 1,2 or 3 and their pharmaceutically acceptable derivatives.

Preferred compounds are those in which X is S and n is 1, i.e., sulconazole, and those in which X is O and n is 1 or 2, i.e., econazole and miconazole. Sulconazole is most preferred.

By "pharmaceutically acceptable derivatives" is meant all acid or base addition salts having significant pharmaceutical utility as anti-inflammatory and antifungal agents. Nitrates are highly preferred.

Sulconazole nitrate is a highly preferred compound.

Mixtures of compounds may be used.

COMPOSITIONS

The compositions useful in the invention are those adapted to the topical administration of one or more of the above compounds to the skin and/or hair of a subject.

Thus, the compositions can be used as creams, gels, ointments, solutions, powders, pastes and the like. Creams and gel formulations are preferred. Gels are highly preferred. One or more forms can be used at the same time during treatment, e.g., creams and powders can be administered together.

The compositions of the invention need not contain any active ingredient(s) other than one or more of the compounds disclosed above. However, such compositions will generally contain suitable quantities of one or more pharmaceutically acceptable excipients to enhance rheology, commercial appeal, packaging and/or handling properties. Accordingly, perfumes, colorants, fillers, thickeners, surfactants, moisturizers, emollients, gelling agents, carriers, preservatives, stabilizers and the like can be used.

When a gel composition is desired, preferred additions include such materials as gelling agents (e.g., hydroxyalkyl celluloses such as hydroxypropyl cellulose), solvents (e.g., monoalcohols, di- or trihydroxy alcohols), emollients (e.g., propylene glycol, isopropyl myristate) and preservatives (e.g., BHT, salicylic acid).

When a cream is to be used, adjuvants such as emulsifiers (e.g., sorbitan esters, polysorbates), water, emollients (e.g., isopropyl myristate, propylene glycol), waxes (e.g., stearyl alcohol, cetyl alcohol) and preservatives (e.g., BHT, ascorbyl palmitate) can be often employed.

A liquid formulation (which may be sprayable) would contain large amounts of one or more carriers such as propylene glycol, water, alcohol(s) and the like.

A powder formulation would contain fillers, such as talc, starch, magnesium stearate and the like and colorants, such as FD & C Red No. 4 and FD & C Yellow No. 5 and the like.

In addition, one or more agents which serve to stabilize the composition may be used. Thus, the use of antioxidants, such as BHT, ascorbyl palmitate, rheological stabilizers such as cellulose derivatives, carbopol and the like can be employed in suitable amounts. Suitable quantities of drugs and excipients to be used in the invention are given in the following table.

Mixtures of the additives discussed above can be used.

| Ingredient | Broad Range | Preferred Range | Highly Preferred Range |
| --- | --- | --- | --- |
| Active compound(s) | 0.01–10% | 0.1–5% | 0.2–2.0% |
| Excipients(s) | 0.01–99.9% | 5–99.9% | 5–99.8% |
| Stabilizer(s) | 0.01–99.9% | 0.01–10% | 0.01–10% |

Some preferred embodiments of the invention contain:

| | |
| --- | --- |
| Imidazole antifungal agent | 0.2–2.0% |
| SD alcohol 40 | 30–65% |
| 1,2,6-hexanetriol | 0–45% |
| 2-ethyl-1,3-hexanediol | 0–40% |
| Isopropyl myristate | 0–40% |
| PPG-20 methyl glucose ether | 0–10% |
| Hydroxypropyl cellulose | 0.1–5% |
| Salicylic acid | 0.1–5% |
| BHT | 0.01–2% |
| 1N NaOH | q.s. to pH 4.0 |

PROCESSES

The processes of the invention involve the treatment of fungal infections and other conditions which have skin inflammation(s) as symptoms. Conditions which may be treated using the invention include tinea pedis, tinea cruris, tinea capitis, cutaneous candidiasis and the like.

The treatment of these or other conditions having inflammatory and/or fungal manifestations involves contacting at least one of the hair or skin of a subject with one or more composition(s) containing the active(s). Thus, the drug is delivered to the host topically, rather than orally or parenterally.

While gels, creams and ointments are preferred formulations from the standpoint of stability, they may not be suitable from a medicinal standpoint. Accordingly, spraying, dusting, painting, etc. may be used to contact the hair or epidermis of a host with the active compound(s).

"Epidermis" includes scalp, as well as non-hairy tissue.

By "host" is meant any mammal. While human subjects are preferred, the invention can be used to treat dogs, cats and other fur-bearing mammals as well.

In general, any area on the surface of a host's body, preferably a human body, may be treated in accordance with the invention. Nasal or ocular use is contemplated, but not preferred.

ADMINISTRATION

It should be appreciated that the wishes and sound medical judgment of a physician skilled in the treatment of a subject's condition may supercede the suggestions below.

The compositions of the invention are applied topically using amounts sufficient enough to cover the affected area of skin. Generally, they will be used about 2 to about 3 times per day, but administration on a once-a-day basis may be sufficient.

Cream and gel formulations, admininstered 2 to 3 times per day for about 28 to about 42 days (i.e., about 4 to about 6 weeks) are preferred. Powders and sprays can be used concommitantly.

Examples

The following examples illustrate the invention.

| Component | Amount, % w/w |
|---|---|
| Example 1 | |
| Sulconazole nitrate | 1.00 |
| SD Alcohol 40 | 52.40 |
| 1,2,6-Hexanetriol | 27.00 |
| 2-Ethyl-1,3-Hexanediol | 7.50 |
| Isopropyl myristate | 7.50 |
| PPG-20 methyl glucose ether | 3.00 |
| Hydroxypropyl cellulose | 0.90 |
| Salicylic acid | 0.50 |
| BHT | 0.20 |
| 1N NaOH | q.s. to PH 4.0 |
| Example 2 | |
| Econazole nitrate | 1.00 |
| SD Alcohol 40 | 52.40 |
| 1,2,6-Hexanetriol | 27.00 |
| 2-Ethyl-1,3-Hexanediol | 7.50 |
| Isopropyl myristate | 7.50 |
| PPG-20 methyl glucose ether | 3.00 |
| Hydroxypropyl cellulose | 0.90 |
| Salicylic acid | 0.50 |
| BHT | 0.50 |
| 1N NaOH | q.s. to PH 4.0 |
| Example 3 | |
| Clotrimazole | 1.00 |
| SD Alcohol 40 | 52.40 |
| 1,2,6-Hexanetriol | 27.00 |
| 2-Ethyl-1,3-Hexanediol | 7.50 |
| Isopropyl myristate | 7.50 |
| PPG-20 methyl glucose ether | 3.00 |
| Hydroxypropyl cellulose | 0.90 |
| Salicylic acid | 0.50 |
| BHT | 0.20 |
| 1N NaOH | q.s. to pH 4.0 |

| Component | Amount, % w/w |
|---|---|
| Example 4 | |
| Sulconazole nitrate | 1.00 |
| SD Alcohol 40 | 50.20 |
| Propylene glycol | 33.00 |
| Isopropyl myristate | 5.00 |
| Water | 5.00 |
| PPG-5-ceteth-20 | 4.20 |
| Hydroxypropyl cellulose | 0.90 |
| Salicylic acid | 0.50 |
| Ascorbyl palmitate | 0.20 |
| 1N NaOH | q.s. to pH 4.0 |
| Example 5 | |
| Sulconazole nitrate | 1.00 |
| SD Alcohol 40 | 35.00 |
| Propylene glycol | 40.00 |
| PPG-5-ceteth-20 | 12.45 |
| Isopropyl myristate | 5.00 |
| Hydroxypropyl cellulose | 0.90 |
| Salicylic acid | 0.50 |
| Ascorbyl palmitate | 0.10 |
| 1N NaOH | q.s. to pH 4.0 |
| Example 6 | |
| Sulconazole nitrate | 1.00 |
| Water | 53.70 |
| Propylene glycol | 25.00 |
| Isopropyl myristate | 6.00 |
| Cetyl alcohol | 3.00 |
| Polysorbate 60 | 2.00 |
| Sorbitan monostearate | 1.00 |
| Glyceryl monostearate SE | 0.30 |
| Ascorbyl palmitate | 0.02 |
| 1N NaOH | q.s. to pH 4.5–5.5 |
| Example 7 | |
| Sulconazole nitrate | 1.00 |
| Propylene glycol | 35.00 |
| Poloxamer 407 | 12.00 |
| Polysorbate 20 | 4.00 |
| BHA | 0.01 |
| Water | q.s. to 100 ml. |
| 1N NaOH | q.s. to pH 4.5–5.5 |

Reasonable variations, such as those which would occur to a skilled artisan, can be made herein without departing from the scope of the invention.

We claim:

1. A composition useful for the topical treatment of inflammations associated with fungal infections of the skin or scalp consisting essentially of:
   (a) about 0.1 to about 10% of at least one compound of formula I or a pharmaceutically acceptable derivative thereof:

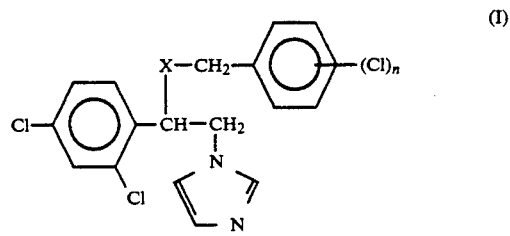

wherein
   x = O or S;
   n = 1, 2 or 3; and
   (b) a pharmaceutically acceptable carrier therefor, wherein the carrier contains a lower alcohol, a trihydroxy alcohol, a dihydroxy alcohol and water.

2. The composition of claim 1 wherein (a) is selected from the group consisting of: sulconazole, econazole, miconazole and mixtures thereof.

3. The compositions of claim 1 wherein (a) is present in an amount of from about 0.2 to about 2% wt/wt.

4. The composition of claim 3 wherein (a) is sulconazole.

5. A process for treating an inflammatory condition associated with a fungal infection of the skin or scalp which comprises the step of:
   contacting the area to be treated with a composition consisting essentially of:
   (a) about 0.1 to about 10% of at least one compound of formula I or a pharmaceutically acceptable derivative thereof:

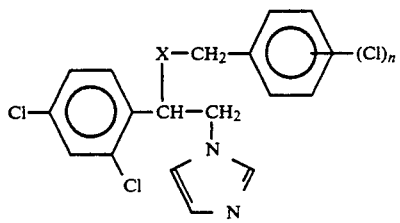

wherein
   X = O or S and
   n = 1, 2 or 3; and
   (b) an alcoholic pharmaceutically acceptable carrier therefor.

6. The process of claim 5 wherein the composition is administered in the form of a gel.

7. A product for treating inflammations associated with fungal infections of the skin or scalp comprising the composition of claim 1.

8. A product for treating inflammations associated with fungal infections of the skin or scalp comprising the composition of claim 4.

9. A process for treating an inflammation on the skin or scalp which comprises contacting the area to be treated with an effective amount of the comprising of claim 1.

10. A composition useful for the topical treatment of inflammations associated with fungal infections of the skin or scalp consisting essentially of: (a) about 0.1 to about 10% of at least one compound of formula I or a pharmaceutically acceptable derivative thereof:

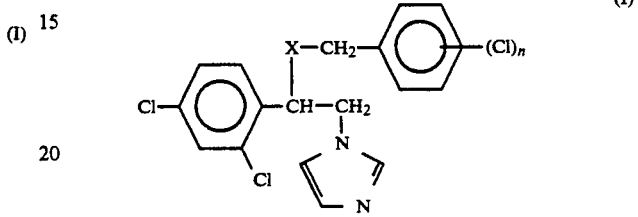

wherein X = O or S; n = 1,2 or 3; and (b) a pharmaceutically acceptable carrier therefor, wherein the carrier contains a lower alcohol, a trihydroxy alcohol, a dihydroxy alcohol and water; and (c) from about 0 to about 50% of emollient(s) and about 0.1 to about 5% of a gelling agent and about 0 to about 5% of preservative(s).

11. A process for treating a fungal inflammation on the skin or scalp which comprises the step of contacting the area to be treated with an effective amount of the composition of claim 10.

* * * * *